United States Patent
Ferrand et al.

(10) Patent No.: US 8,080,063 B2
(45) Date of Patent: Dec. 20, 2011

(54) GLENOID COMPONENT WITH AN ANATOMICALLY OPTIMIZED KEEL

(75) Inventors: Lucile Ferrand, Montbonnot (FR); Irene Ferrari, St Vincent de Mercuze (FR); Yves-Alain Ratron, Grenoble (FR)

(73) Assignee: Tornier SAS, Saint Ismier (FR)

( * ) Notice: Subject to any disclaimer, the term of this patent is extended or adjusted under 35 U.S.C. 154(b) by 247 days.

(21) Appl. No.: 11/735,027

(22) Filed: Apr. 13, 2007

(65) Prior Publication Data

US 2007/0244564 A1    Oct. 18, 2007

(30) Foreign Application Priority Data

Apr. 13, 2006    (FR) ...................................... 06 03291

(51) Int. Cl.
*A61F 2/40*    (2006.01)
(52) U.S. Cl. .................. 623/19.13; 623/19.11
(58) Field of Classification Search ............... 623/19.11, 623/19.12, 19.13, 20.14, 20.15, 20.32, 20.34
See application file for complete search history.

(56) References Cited

U.S. PATENT DOCUMENTS

| | | | |
|---|---|---|---|
| 3,694,820 A | 10/1972 | Scales et al. |
| 3,815,157 A | 6/1974 | Skorecki et al. |
| 3,842,442 A | 10/1974 | Kolbel |
| 3,864,758 A | 2/1975 | Yakich |
| 3,869,730 A | 3/1975 | Skobel |
| 3,916,451 A | 11/1975 | Buechel et al. |
| 3,978,528 A | 9/1976 | Crep |
| 3,979,778 A | 9/1976 | Stroot |
| 3,992,726 A | 11/1976 | Freeman et al. |
| 4,003,095 A | 1/1977 | Gristina |
| 4,030,143 A | 6/1977 | Elloy et al. |
| 4,040,131 A | 8/1977 | Gristina |
| 4,054,955 A | 10/1977 | Seppo |
| 4,135,517 A | 1/1979 | Reale |
| 4,179,758 A | 12/1979 | Gristina |
| 4,206,517 A | 6/1980 | Pappas et al. |
| 4,261,062 A | 4/1981 | Amstutz et al. |
| 4,550,450 A | 11/1985 | Kinnett |

(Continued)

FOREIGN PATENT DOCUMENTS

CH    426096    12/1966

(Continued)

OTHER PUBLICATIONS

"Aequalis-Fracture Suture Technique in 5 Steps," Tornier, Inc.

(Continued)

*Primary Examiner* — David Isabella
*Assistant Examiner* — Joshua Levine
(74) *Attorney, Agent, or Firm* — Faegre & Benson LLP (57) ABSTRACT

A glenoid component for a shoulder prosthesis adapted to be mounted in a glenoid cavity of a shoulder. An elongated keel adapted to engage with the glenoid cavity is attached to the internal surface of the base. The keel extends along a longitudinal axis of the base. The keel includes various configurations of transverse members extending away from the longitudinal axis. The surgeon selects a glenoid component with a keel and transverse member configuration that is anatomically optimized for the patient. Glenoid components properly optimized provide mechanical strength and stability superior to prior art devices. The glenoid components disclosed herein are particularly well suited for use in an anatomical total shoulder prosthesis, but may are also suited to partial shoulder prostheses and reverse shoulder prostheses.

21 Claims, 5 Drawing Sheets

U.S. PATENT DOCUMENTS

| | | |
|---|---|---|
| 4,693,723 A | 9/1987 | Gabard |
| 4,822,370 A | 4/1989 | Schelhas |
| 4,846,840 A | 7/1989 | Leclercq et al. |
| 4,865,605 A | 9/1989 | Dines et al. |
| 4,865,609 A | 9/1989 | Roche |
| 4,892,549 A | 1/1990 | Figgie, III et al. |
| 4,919,670 A | 4/1990 | Dale et al. |
| 4,957,510 A | 9/1990 | Cremascoli |
| 4,963,155 A | 10/1990 | Lazzeri et al. |
| 5,032,132 A | 7/1991 | Matsen, III et al. |
| 5,080,673 A | 1/1992 | Burkhead et al. |
| 5,080,685 A | 1/1992 | Bolesky et al. |
| 5,127,920 A | 7/1992 | MacArthur |
| 5,135,529 A | 8/1992 | Paxson et al. |
| 5,163,961 A | 11/1992 | Harwin |
| 5,171,289 A | 12/1992 | Tornier |
| 5,181,928 A | 1/1993 | Bolesky et al. |
| 5,192,329 A | 3/1993 | Christie et al. |
| 5,201,882 A | 4/1993 | Paxson |
| 5,206,925 A | 4/1993 | Nakazawa et al. |
| 5,222,984 A | 6/1993 | Forte |
| 5,261,914 A | 11/1993 | Warren |
| 5,314,479 A | 5/1994 | Rockwood, Jr. et al. |
| 5,314,485 A | 5/1994 | Judet |
| 5,314,487 A | 5/1994 | Schryver et al. |
| 5,326,359 A | 7/1994 | Oudard |
| 5,330,531 A | 7/1994 | Capanna |
| 5,358,526 A | 10/1994 | Tornier |
| 5,383,936 A | 1/1995 | Kubein-Meesenburg et al. |
| 5,405,399 A | 4/1995 | Tornier |
| 5,425,779 A | 6/1995 | Schlosser et al. |
| 5,429,639 A | 7/1995 | Judet |
| 5,443,519 A | 8/1995 | Averill et al. |
| 5,458,650 A | 10/1995 | Carret et al. |
| 5,462,563 A | 10/1995 | Shearer et al. |
| 5,505,731 A | 4/1996 | Tornier |
| 5,507,817 A | 4/1996 | Craig et al. |
| 5,507,818 A | 4/1996 | McLaughlin |
| 5,507,824 A | 4/1996 | Lennox |
| 5,509,934 A * | 4/1996 | Cohen ........................ 623/20.32 |
| 5,549,682 A | 8/1996 | Roy |
| 5,580,352 A | 12/1996 | Sekel |
| 5,591,168 A | 1/1997 | Judet et al. |
| 5,662,651 A | 9/1997 | Tornier et al. |
| 5,676,702 A | 10/1997 | Ratron |
| 5,702,447 A | 12/1997 | Walch et al. |
| 5,702,457 A | 12/1997 | Walch et al. |
| 5,702,478 A | 12/1997 | Tornier |
| 5,702,486 A | 12/1997 | Craig et al. |
| 5,723,018 A | 3/1998 | Cyprien et al. |
| 5,728,161 A | 3/1998 | Camino et al. |
| 5,741,335 A | 4/1998 | Gerber et al. |
| 5,755,807 A | 5/1998 | Anstaett et al. |
| 5,766,256 A | 6/1998 | Oudard et al. |
| 5,800,551 A | 9/1998 | Williamson et al. |
| 5,824,106 A | 10/1998 | Fournol |
| 5,879,395 A | 3/1999 | Tornier et al. |
| 5,879,405 A | 3/1999 | Ries et al. |
| 5,902,340 A | 5/1999 | White et al. |
| 5,910,171 A | 6/1999 | Kummer et al. |
| 5,928,285 A | 7/1999 | Bigliani et al. |
| 5,944,758 A | 8/1999 | Mansat et al. |
| 5,961,555 A | 10/1999 | Huebner |
| 5,984,927 A | 11/1999 | Wenstrom, Jr. et al. |
| 6,015,437 A | 1/2000 | Stossel |
| 6,033,439 A | 3/2000 | Camino et al. |
| 6,045,582 A | 4/2000 | Prybyla |
| 6,045,583 A | 4/2000 | Gross et al. |
| 6,102,953 A | 8/2000 | Huebner |
| 6,129,764 A | 10/2000 | Servidio |
| 6,162,254 A | 12/2000 | Timoteo |
| 6,165,224 A | 12/2000 | Tornier |
| 6,168,629 B1 | 1/2001 | Timoteo |
| 6,171,341 B1 | 1/2001 | Boileau et al. |
| 6,183,519 B1 | 2/2001 | Bonnin et al. |
| 6,197,062 B1 | 3/2001 | Fenlin |
| 6,197,063 B1 | 3/2001 | Dews |
| 6,203,575 B1 | 3/2001 | Farey |
| 6,206,925 B1 | 3/2001 | Tornier |
| 6,228,120 B1 | 5/2001 | Leonard et al. |
| 6,267,767 B1 | 7/2001 | Stroble et al. |
| 6,283,999 B1 | 9/2001 | Rockwood, Jr. |
| 6,299,646 B1 | 10/2001 | Chambat et al. |
| 6,312,467 B1 | 11/2001 | McGee |
| 6,328,758 B1 | 12/2001 | Tornier et al. |
| 6,334,874 B1 | 1/2002 | Tornier et al. |
| 6,364,910 B1 | 4/2002 | Shultz et al. |
| 6,368,352 B1 | 4/2002 | Camino et al. |
| 6,368,353 B1 | 4/2002 | Arcand |
| 6,379,387 B1 | 4/2002 | Tornier |
| 6,398,812 B1 | 6/2002 | Masini |
| 6,406,495 B1 | 6/2002 | Schoch |
| 6,406,496 B1 | 6/2002 | Rüter |
| 6,436,144 B1 | 8/2002 | Ahrens |
| 6,436,147 B1 | 8/2002 | Zweymuller |
| 6,454,809 B1 | 9/2002 | Tornier |
| 6,458,136 B1 | 10/2002 | Allard et al. |
| 6,475,243 B1 | 11/2002 | Sheldon et al. |
| 6,488,712 B1 | 12/2002 | Tornier et al. |
| 6,494,913 B1 | 12/2002 | Huebner |
| 6,506,214 B1 | 1/2003 | Gross |
| 6,508,840 B1 | 1/2003 | Rockwood, Jr. et al. |
| 6,514,287 B2 | 2/2003 | Ondrla et al. |
| 6,520,994 B2 | 2/2003 | Nogarin |
| 6,530,957 B1 | 3/2003 | Jack |
| 6,540,770 B1 | 4/2003 | Tornier et al. |
| 6,558,425 B2 | 5/2003 | Rockwood |
| 6,569,202 B2 | 5/2003 | Whiteside |
| 6,582,469 B1 | 6/2003 | Tornier |
| 6,589,281 B2 | 7/2003 | Hyde, Jr. |
| 6,599,295 B1 | 7/2003 | Tornier et al. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,673,115 B2 | 1/2004 | Resch et al. |
| 6,679,916 B1 | 1/2004 | Frankle et al. |
| 6,736,851 B2 | 5/2004 | Maroney et al. |
| 6,746,487 B2 | 6/2004 | Scifert et al. |
| 6,749,637 B1 | 6/2004 | Bahler |
| 6,755,866 B2 | 6/2004 | Southworth |
| 6,761,740 B2 | 7/2004 | Tornier |
| 6,767,368 B2 | 7/2004 | Tornier |
| 6,780,190 B2 | 8/2004 | Maroney |
| 6,783,549 B1 | 8/2004 | Stone et al. |
| 6,790,234 B1 | 9/2004 | Frankle |
| 6,802,864 B2 | 10/2004 | Tornier |
| 6,824,567 B2 | 11/2004 | Tornier et al. |
| 6,863,690 B2 | 3/2005 | Ball et al. |
| 6,875,234 B2 | 4/2005 | Lipman et al. |
| 6,887,277 B2 | 5/2005 | Rauscher et al. |
| 6,890,357 B2 | 5/2005 | Tornier |
| 6,890,358 B2 | 5/2005 | Ball et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,011,686 B2 | 3/2006 | Ball et al. |
| 7,033,396 B2 | 4/2006 | Tornier |
| 7,066,959 B2 | 6/2006 | Errico |
| 7,108,719 B2 | 9/2006 | Horber |
| 7,166,132 B2 | 1/2007 | Callaway et al. |
| 7,169,184 B2 | 1/2007 | Dalla Pria |
| 7,175,663 B1 | 2/2007 | Stone |
| 7,195,645 B2 | 3/2007 | Disilvestro et al. |
| 7,238,207 B2 | 7/2007 | Blatter et al. |
| 7,238,208 B2 | 7/2007 | Camino et al. |
| 7,297,163 B2 | 11/2007 | Huebner |
| 7,309,360 B2 | 12/2007 | Tornier et al. |
| 7,329,284 B2 | 2/2008 | Maroney et al. |
| 7,338,498 B2 | 3/2008 | Long et al. |
| 7,338,528 B2 | 3/2008 | Stone et al. |
| 2001/0032021 A1 | 10/2001 | McKinnon |
| 2001/0047210 A1 | 11/2001 | Wolf |
| 2001/0049561 A1 | 12/2001 | Dews et al. |
| 2002/0032484 A1 | 3/2002 | Hyde, Jr. |
| 2002/0099381 A1 | 7/2002 | Maroney |
| 2002/0138148 A1 | 9/2002 | Hyde, Jr. |
| 2002/0143402 A1 | 10/2002 | Steinberg |

| | | |
|---|---|---|
| 2002/0151982 A1 | 10/2002 | Masini |
| 2003/0009170 A1 | 1/2003 | Tornier |
| 2003/0009171 A1 | 1/2003 | Tornier |
| 2003/0028198 A1 | 2/2003 | Tornier et al. |
| 2003/0060884 A1* | 3/2003 | Fell et al. .................. 623/14.12 |
| 2003/0097183 A1 | 5/2003 | Rauscher et al. |
| 2004/0006392 A1 | 1/2004 | Grusin et al. |
| 2004/0034431 A1 | 2/2004 | Maroney et al. |
| 2004/0064189 A1 | 4/2004 | Maroney et al. |
| 2004/0133276 A1 | 7/2004 | Lang et al. |
| 2004/0134821 A1 | 7/2004 | Tornier |
| 2004/0138754 A1 | 7/2004 | Lang et al. |
| 2004/0148033 A1 | 7/2004 | Schroeder |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210220 A1 | 10/2004 | Tornier |
| 2004/0210317 A1 | 10/2004 | Maroney et al. |
| 2004/0215200 A1 | 10/2004 | Tornier et al. |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0267370 A1 | 12/2004 | Ondria |
| 2005/0008672 A1 | 1/2005 | Winterbottom et al. |
| 2005/0015154 A1 | 1/2005 | Lindsey et al. |
| 2005/0043805 A1 | 2/2005 | Chudik |
| 2005/0049709 A1* | 3/2005 | Tornier .................. 623/19.13 |
| 2005/0055102 A1 | 3/2005 | Tornier et al. |
| 2005/0065612 A1 | 3/2005 | Winslow |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113931 A1 | 5/2005 | Horber |
| 2005/0119531 A1 | 6/2005 | Sharratt |
| 2005/0143829 A1 | 6/2005 | Ondria et al. |
| 2005/0165490 A1 | 7/2005 | Tornier |
| 2005/0177241 A1 | 8/2005 | Angibaud et al. |
| 2005/0197708 A1 | 9/2005 | Stone et al. |
| 2005/0203536 A1 | 9/2005 | Laffargue et al. |
| 2005/0209700 A1 | 9/2005 | Rockwood et al. |
| 2005/0216092 A1 | 9/2005 | Marik et al. |
| 2005/0230197 A1 | 10/2005 | Jedele |
| 2005/0251263 A1 | 11/2005 | Forrer et al. |
| 2005/0256584 A1 | 11/2005 | Farrar |
| 2005/0261775 A1 | 11/2005 | Baum et al. |
| 2005/0267590 A1 | 12/2005 | Lee |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0015185 A1 | 1/2006 | Chambat et al. |
| 2006/0020344 A1 | 1/2006 | Shultz et al. |
| 2006/0030946 A1 | 2/2006 | Ball et al. |
| 2006/0116772 A1* | 6/2006 | Haidukewych ............ 623/20.34 |
| 2006/0173457 A1 | 8/2006 | Tornier |
| 2006/0235538 A1 | 10/2006 | Rochetin et al. |
| 2006/0241775 A1 | 10/2006 | Buss |
| 2007/0043265 A1 | 2/2007 | Rochetin |
| 2007/0225817 A1 | 9/2007 | Reubelt et al. |
| 2007/0225818 A1 | 9/2007 | Reubelt et al. |
| 2007/0225821 A1 | 9/2007 | Reubelt et al. |
| 2007/0250174 A1 | 10/2007 | Tornier et al. |

FOREIGN PATENT DOCUMENTS

| | | |
|---|---|---|
| CH | 507704 | 5/1971 |
| DE | 19509037 | 9/1996 |
| DE | 19630298 | 1/1998 |
| EP | 0257359 | 3/1988 |
| EP | 0299889 | 1/1989 |
| EP | 0524857 | 1/1993 |
| EP | 0549480 | 6/1993 |
| EP | 0599429 | 6/1994 |
| EP | 0617934 | 10/1994 |
| EP | 0664108 | 7/1995 |
| EP | 0679375 | 11/1995 |
| EP | 0712617 | 5/1996 |
| EP | 0715836 | 6/1996 |
| EP | 0797964 | 10/1997 |
| EP | 0807426 | 11/1997 |
| EP | 0809986 | 12/1997 |
| EP | 0864306 | 9/1998 |
| EP | 0903127 | 3/1999 |
| EP | 0903128 | 3/1999 |
| EP | 0927548 | 7/1999 |
| EP | 1062923 | 12/2000 |
| EP | 1064890 | 1/2001 |
| EP | 1195149 | 4/2002 |
| EP | 1380274 | 1/2004 |
| EP | 1402854 | 3/2004 |
| FR | 2248820 | 5/1975 |
| FR | 2545352 | 11/1984 |
| FR | 2574283 | 6/1986 |
| FR | 2652498 | 4/1991 |
| FR | 2664809 | 1/1992 |
| FR | 2699400 | 6/1994 |
| FR | 2721200 | 12/1995 |
| FR | 2726994 | 5/1996 |
| FR | 2737107 | 1/1997 |
| FR | 2835425 | 8/2003 |
| FR | 2836039 | 8/2003 |
| FR | 2859099 | 3/2005 |
| SU | 749392 | 7/1980 |
| WO | 9107932 | 6/1991 |
| WO | 9309733 | 5/1993 |
| WO | 9617553 | 6/1996 |
| WO | 9846172 | 10/1998 |
| WO | 9949792 | 10/1999 |
| WO | 9965413 | 12/1999 |
| WO | 0015154 | 3/2000 |
| WO | 0041653 | 7/2000 |
| WO | 0147442 | 7/2001 |
| WO | 0239931 | 5/2002 |
| WO | 0239933 | 5/2002 |
| WO | 02067821 | 9/2002 |
| WO | 03005933 | 1/2003 |
| WO | WO 03/094806 | 11/2003 |
| WO | WO 2007/109319 | 2/2007 |
| WO | WO 2007/109291 | 9/2007 |
| WO | WO 2007/109340 | 9/2007 |

OTHER PUBLICATIONS

"Aequalis-Fracture Shoulder Prosthesis—Surgical Technique," Tornier, Inc.

"Aequalis® Press-Fit Shoulder Prosthesis—Surgical Technique," Tornier, Inc.

"Anatomical Shoulder™—Cemented Shoulder Prosthesis Product Information and Surgical Technique," Sulzer Medica, 2000.

"Anatomical Shoulder™ System Surgical Technique—Removable head option for improved surgical results," Zimmer, Inc., 2004.

Bigliani/Flatow®—The Complete Shoulder Solution, 4-Part Fracture of the Humerus Surgical Technique, Zimmer, Inc., 2000.

"Bio-Modular®/ Bi-Polar Shoulder Arthroplasty," Biomet, Inc., 1997.

"Bio-Modular® Choice, Shoulder System," Biomet Orthopedics, Inc., 2004.

"Bio-Modular Total Shoulder Surgical Technique," Biomet Orthopedics, Inc., 2001.

"Copeland™ Humeral Resurfacing Head," Biomet Orthopedics, Inc., 2001.

"Global C.A.P.™ Surgical technique, resurfacing humeral head implant," DePuy International, Ltd., 2004.

Boileau, et al. "Adaptability and modularity of shoulder prosthese," *Maitrise Orthopédique*, https://www.maitriseorthop.com/corpusmaitri/orthopaedic/prothese_epaule_orthop/boileau_us.shtml, Jan. 3, 2006.

Boileau, et al. "Arthroscopic Repair of Full-Thickness Tears of the Supraspinatus: Does the tendon really hear?," *The Journal of Bone and Joint Surgery, Inc.*, pp. 1229-1240, 2005.

"Design Rationale," Latitude®.

Klein, Travis J., et al. "Mechanically favorable bone remodeling in rotator cuff arthropathy patients with good function," *Minneapolis Sports Medicine Center and University of Minnesota*.

Mansat, Michel, "Neer 3™, Surgical Technique for Fractrures," Smith & Nephew, 2000.

Molé, M.D., et al., "Aequalis-Reversed™ Shoulder Prosthesis, Surgical Technique," Tornier, Inc.

Nicholson, Gregory P., "Arthroplasty and Rotator Cuff Deficiency," Chapter 7, pp. 149-166.

"Offset Head, Bio-Modular® Total Shoulder," Biomet, Inc. 2000.

"The Foundation® Total Shoulder System," Encore Surgical.

"The Townley Modular Shoulder, Design by Reason," Biopro, Inc.

Zimmer® Bigliani/Flatow®—The Complete Shoulder Solution, Total Shoulder Arthroplasty Surgical Technique, Zimmer, Inc., 2003.

"Zimmer® Shoulder Retractors,"Zimmer, Inc., 2000.

"Anatomic Glenoid, Surgical Technique," Smith & Nephew, 2000.

"Anatomical ShoulderTM System—The new removable head option," Zimmer Inc., 2004.

"Delta CTA™ Reverse Shoulder Prosthesis," DePuy International, Ltd., 2004.

Cofield, M.D., Robert H. "Cofield[2] Total Shoulder System, Surgical Technique," Smith & Nephew, 1997.

"Aequalis®-Glenoid Keeled and Pegged—Surgical Technique," Tornier, Inc.

"Bigliani/Flatow®—The Complete Shoulder Solution, Designed by Shoulder Surgeons for Shoulder Surgery," Zimmer, Inc., 2001.

"Tornier Surgical Technique Addendum, Tornier Aequalis® Reversed Hemi-Adaptor Technique," Tornier, Inc., Aug. 8, 2005.

"Tornier Surgical Technique Addendum, Aequalis® Reversed Shoulder Polyethylene Insert," Tornier, Inc., Aug. 8, 2005.

Beuchel M.D., Frederick F. "Beuchel-Pappas™ Modular Salvage Shoulder System," Endotec, Inc., 2000.

Beuchel M.D., Frederick F. "Beuchel-Pappas™ Resurfacing Shoulder System," Endotec, Inc., 2000.

Beuchel M.D., Frederick F. "Beuchel-Pappas™ Total Shoulder System," Endotec, Inc., 2000.

Hertel M.D., PD, Ralph. "Technical considerations for implantation of EPOCA glenoid components (Leseprobe)," *Epoca Newsletter*, May 14, 2001.

Apoil, André "A Condyle for the Rotator Cuff Muscles, the total shoulder prosthesis," Aesculap®, 1994.

"Tornier Aequalis® Reversed 2 Prong Capsular Retractor," Tornier, Inc., Oct. 8, 2005.

"Tornier Aequalis® Reversed Shoulder G2 Baseplate," Tornier, Inc., Oct. 8, 2005.

Boileau et al., U.S. Appl. No. 12/020,913, entitled "Method and Apparatus for Fitting a Shoulder Prosthesis" filed Jan. 28, 2008.

John M. Fenlin Jr., M.D., Symposium on Surgery of the Shoulder, "Total Glenohumeral Joint Replacement," Orthopedic Clinics of North America, vol. 6, No. 2, Apr. 1975, pp. 565-583.

Rochetin et al., U.S. Appl. No. 11/401,415, entitled "Surgical Apparatus for Implantation of a Partial or Total Knee Prosthesis", filed Apr. 11, 2006.

Rochetin et al., U.S. Appl. No. 11/670,274, entitled "Offset Stem Tibial Implantation", filed Feb. 1, 2007.

Ratron et al., U.S. Appl. No. 11/626,735, entitled "Surgical Instrumentation Kit for Inserting an Ankle Prosthesis", filed Jan. 24, 2007.

Bicknell, et al., "Does keel size, the use of screws, and the use of bone cement affect fixation of a metal glenoid implant?", J Shoulder Elbow Surg, 2003, vol. 12, No. 3, pp. 268-275.

\* cited by examiner

GLENOID COMPONENT WITH AN ANATOMICALLY OPTIMIZED KEEL

CROSS REFERENCE TO RELATED APPLICATIONS

The present application claims priority to French application No. 0603291 filed on Apr. 13, 2006.

FIELD OF THE INVENTION

The present invention relates to a glenoid component with an anatomically optimized keeled for use in total or partial shoulder prosthesis, and to a set of such glenoid components.

BACKGROUND OF THE INVENTION

In the field of shoulder prostheses it is known, for example from U.S. Publication No. 2005/0049709 (based on FR-A-2 859 099), to use a glenoid component that includes a base capable of resting against the patient's glenoid cavity. The base is combined with a fixing member intended to penetrate deeply into this glenoid cavity in order to connect it securely to the aforementioned component.

U.S. Publication No. 2005/0049709 teaches a fixing member is in the form of a keel that includes a main longitudinal axis. The base has a concave surface opposite the keel that is capable of cooperating with a totally hemispherical head of a humeral component of the shoulder prosthesis. For satisfactory implantation, from the anatomical point of view, of the glenoid component in the glenoid cavity the keel of this component has a length which is less than that of the base resting against the glenoid cavity. In addition, the keel is slightly tapered so that the length of its free end is less than the length of this keel in the region of its zone of connection to the base.

U.S. Publication No. 2005/0261775 also discloses an alternative solution in which the aforementioned fixing member is formed by a solid stud. As in the case of the aforementioned keel, this stud has dimensions that are less than these in the region of its zone of connection to the base, for anatomical reasons. A stud of this type is relatively invasive toward the patient. Its use necessitates the removal of a significant portion of the patient's bone stock, which is detrimental in particular when refitting the implant.

U.S. Pat. No. 3,869,730 discloses a shoulder prosthesis comprising a glenoid component that is equipped with a first diametral plate as well as two half plates extending transversely to this main plate. However, these various plates for fixing the component in the glenoid cavity are not anatomical since their dimensions are identical to those of the base and, consequently, they are capable of leading to at least partial destruction of the glenoid cavity. In this respect, it will be noted that these plates cannot be considered as a fixing keel, as mentioned above.

Bicknell et al., *Does Keel Size, The Use Of Screw, And The Use Of Bone Cement Affect Fixation of A Metal Glenoid Implant?*, 12 J of Shoulder Elbow Surg. 268 (2003) discloses a symmetrical blade-type, cross-keeled glenoid components. The five cross-keeled glenoid components tested varied only in size, not in the configuration had keel. The article concludes that the size of the keel was not found to have a significant effect on the stability of the glenoid components, as measured by the variable of contra-lateral lift-off. The article also concludes that supplemental screw fixation significantly improved implant fixation relative to the un-cemented keel, regardless of keel size. The keel was not optimized to the patient's anatomy.

BRIEF SUMMARY OF THE INVENTION

The various embodiments disclosed herein are directed to a glenoid component for a shoulder prosthesis adapted to be mounted in a glenoid cavity of a shoulder. An elongated keel adapted to engage with the glenoid cavity is attached to the internal surface of the base. The keel extends along a longitudinal axis of the base. The keel includes various configurations of transverse members extending away from the longitudinal axis. The surgeon selects a glenoid component with a keel and transverse member configuration that is anatomically optimized for the patient. Such glenoid components properly optimized for the patient provide mechanical strength and stability superior to prior art devices. The glenoid components disclosed herein are particularly well suited for use in an anatomical total shoulder prosthesis, but many are also suited to partial shoulder prostheses and reverse shoulder prostheses.

Optimizing the glenoid component for the patient's anatomy has the advantage of minimizing rocking of the glenoid component and reduces loosening of the glenoid component from the glenoid cavity. In addition, the keel and transverse members increase the rigidity of the base of the glenoid component. This structural advantage allows micromovements to be reduced, owing to the improvement in the primary grip of the entire component. Finally, transverse members anatomically optimized resist shearing forces applied to the glenoid component better than conventional glenoid components.

Anatomical optimization may include selecting a glenoid component with transverse members configured, for example, with heights less than a height of the keel; at non-orthogonal angles relative to the longitudinal axis; integrally formed with, or connected to, the keel; symmetrical or asymmetrical arranged about the longitudinal axis; located at a median region, an intermediate region or an end region of the keel; with a gap between one or more of the transverse members and the keel; with anchor members oriented generally parallel to the longitudinal axis and attached to at least one of the transverse members or the keel; at least one generally planar surface located on the transverse members oriented generally parallel to the external articulating surface; and/or with holes in the transverse members. Variations in the keel configuration may also be incorporated in the set of glenoid components. Depending on the patient's anatomy, determined by the surgeon before and/or during surgery, it is possible to select a glenoid component that is anatomically optimized for the patient.

The invention relates to a total shoulder prosthesis comprising a glenoid component as defined hereinbefore, as well as a humeral component capable of cooperating with this glenoid component.

BRIEF DESCRIPTION OF THE SEVERAL VIEWS OF THE DRAWING

The invention will be understood better and further advantages thereof will emerge more clearly from the following description which is given merely as a non-limiting example with reference to the accompanying drawings, in which.

DETAILED DESCRIPTION OF THE INVENTION

Figure 1:
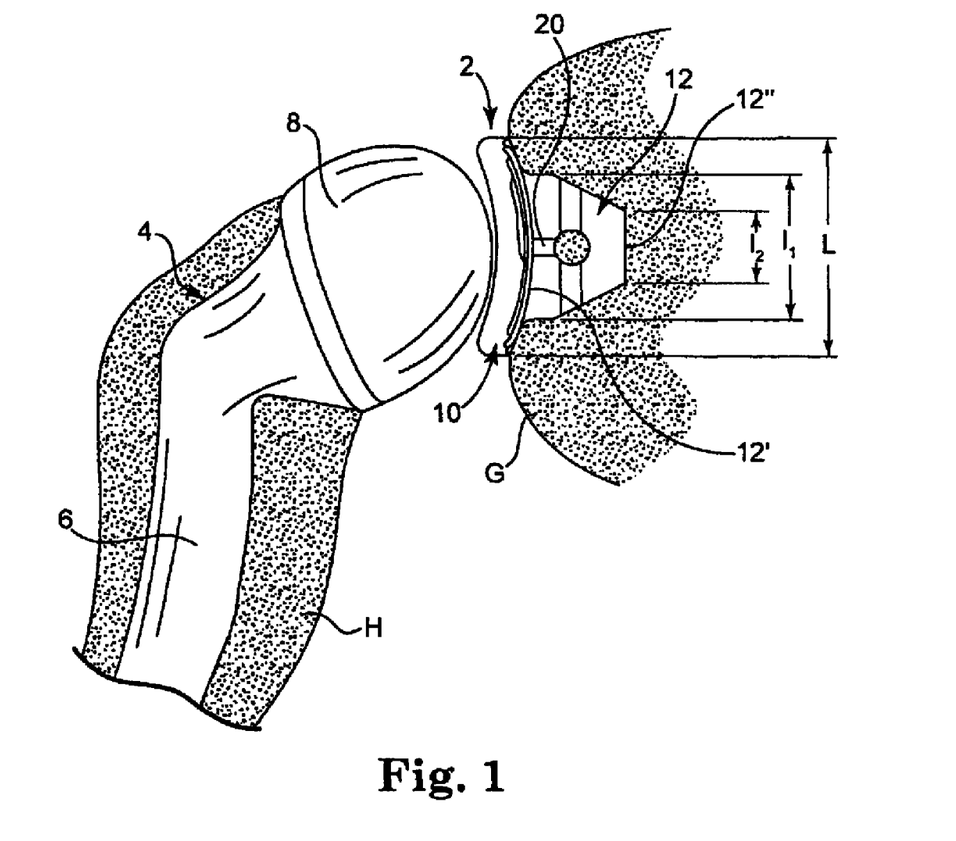
FIG. 1 is a schematic view of a shoulder prosthesis including a glenoid component with a cross-keeled base in accordance with an embodiment of the present invention.

The total shoulder prosthesis shown in FIG. 1 includes a glenoid component 2 integrally connected to the glenoid cavity G of a shoulder as well as a humeral component 4 integrally connected to the corresponding humerus H. This humeral component 4 includes a stem 6 intended to be fixed in the medullary canal of the humerus H, as well as a hemispherical head 8 including a convex surface.

The glenoid component 2 includes a base 10 having with an external surface or articular surface $10_1$ opposite the glenoid cavity. In the illustrated embodiment, the external surface $10_1$, includes a concave profile that is intended to cooperate in the anatomical manner with the head 8 of the humeral component 4. The glenoid component 2 can be made of metal, plastics material, ceramic, or composites thereof, or of any other suitable biocompatible material.

Internal surface $10_2$ of the base 10 rests against the glenoid cavity G of the shoulder. For this purpose, this internal surface $10_2$ is optionally provided with serrations $10_3$ to facilitate implantation of the base 10. In some embodiments, the serrations $10_3$ increase anterior/posterior stability of the glenoid component 2. The base 10 includes keel 12 extending along longitudinal axis X-X. The keel 12 preferably includes a longitudinal dimension or length that is greater than its transverse dimension or width.

Axis Y-Y corresponds to the width of the keel and axis Z-Z corresponding to its thickness respectively. The axes X-X, Y-Y, and Z-Z are preferably orthogonal to each other. As used herein, "keel" refers to an elongated ridge or upstanding structure attached to a glenoid component with a length oriented along a longitudinal axis of the glenoid component. The keel preferably has a length greater than its width. The keel may have a length greater than, less than, or the same as the base of the glenoid component. The keel typically has generally planer sides, which may include a variety of protrusions, recesses, anchor members, and holes. The keel is adapted to engage with a glenoid cavity of a shoulder to increase mechanical strength and stability.

The length $1_1$ of the keel 12, in the region of its zone of connection 12' to the base 2, is less than the length L of the base 2. In addition, the length $1_2$ of this keel 12, in the region of its free end 12", is less than the above-defined length $1_1$, so this keel has a slightly tapered profile. These different lengths L, $1_1$ and $1_2$, which are taken along the main axis X-X, are illustrated in FIG. 1.

Figure 2:
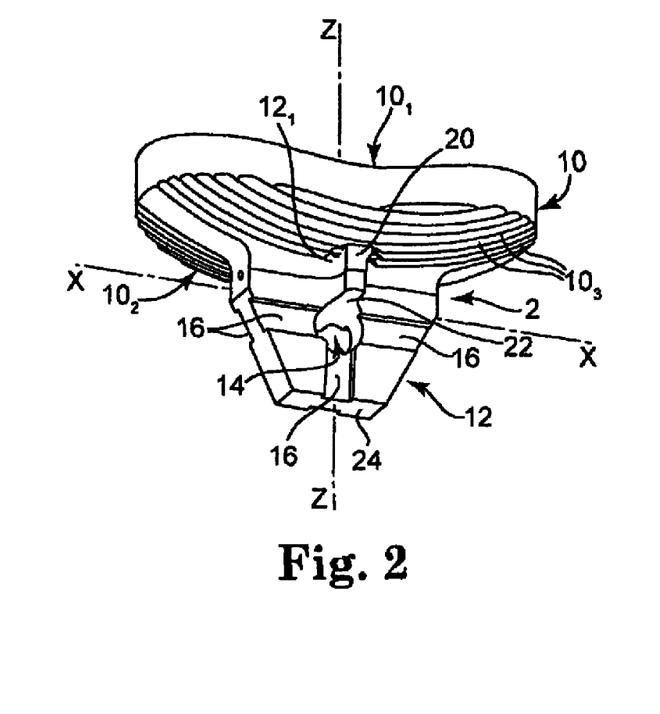
FIG. 2 is a perspective view of the glenoid component of FIG. 1.

As illustrated in FIG. 2, the keel 12 includes transverse hole 14, allowing the creation of a cement bridge for fixing the component, if it is cemented. If the component is not cemented, the hole 14 is likely to allow the creation of a bone bridge. In another embodiment, the hole 14 may be used to receive one or more fasteners, such as bone screws.

Notches 16 are preferably formed on each of the lateral surfaces of this keel 12. The notches 16 preferably extend from the walls of the hole 14, defining substantially the shape of a T. The function of these notches is to allow satisfactory attachment of the component 2 to the glenoid cavity G, either by engagement with cement or as regions for subsequent bone in-growth.

Figure 3:
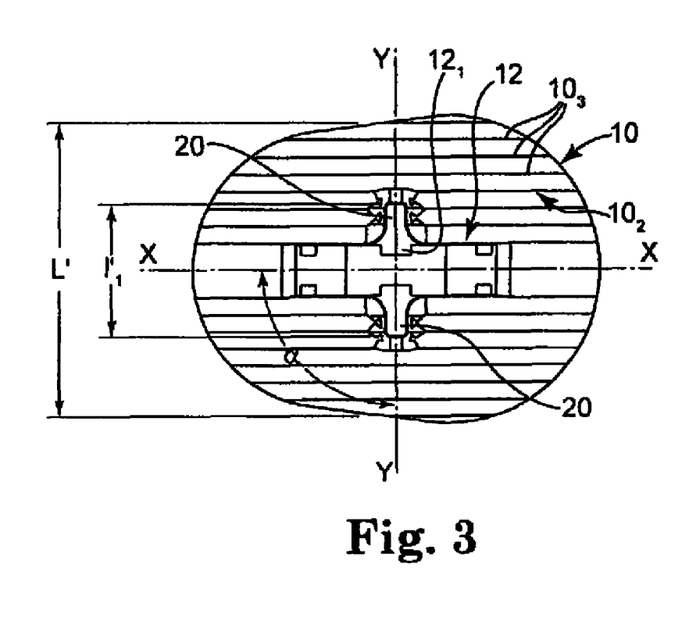
FIG. 3 is a plan view of the glenoid component of FIG. 2.

In the illustrated embodiment, two transverse members 20 extend laterally from the keel 12 while forming an angle α relative to the longitudinal axis X-X, as shown in particular in FIG. 3. In the illustrated example, this angle α is approximately 90° but, as a variation, it can be between 30 and 150°, in particular between 45 and 135° (see e.g., FIG. 7).

In the embodiment of FIG. 2 the transverse members 20 have a height measured along the Z-Z axis less than a height of the keel 12. In one embodiment, the transverse members 20 have a height of about one half the height of the keel 12. In an alternate embodiment, the transverse members 20 may have a height approximately equal to the height of the keel 12 (see e.g., FIG. 4). As used herein, "transverse member" refers to a structure on a glenoid component extending away from a longitudinal axis of a keel. The terms "transverse" or "transversely" should not be interpreted to imply right angles, since the transverse member may extend away from the keel at a variety of angles. The transverse member may be connect to or formed integrally with the keel, or may optionally be spaced apart from the keel.

The keel 12 and the transverse members 20 preferably include generally planar surfaces 22 and 24, both oriented to engage with the glenoid cavity. In the preferred embodiment, the surfaces 22 and 24 are generally parallel to the external surface $10_1$. The surfaces 22 and 24 act in concert with the internal surface $10_2$ of the base 10 to resist compressive forces applied to the external surface $10_1$ by the humeral head 8. By contrast, the blade-type keel disclosed in Bicknell et al. provides minimal resistance to such compressive forces. If the glenoid component disclosed in Bicknell et al. is driven further into the glenoid cavity by such forces, instability will result.

With reference to this FIG. 3, it is noted that the transverse members 20 extend only over a portion of the base 2. In other words, the distance $1'_1$ separating the two opposing ends of these transverse members 20 is much less than the width L' of the base 2, as measured along the Y-Y axis.

In the illustrated example, moreover, the transverse members 20 extend symmetrically about the axis X-X. Alternatively, the transverse members can be arrange asymmetrically about the axis X-X (see e.g., FIG. 8). In a variation, a single transverse member may be used. In an additional variation, a number of transverse members greater than one may be used on at least one of the two sides of the component (see e.g., FIG. 7). Finally, the dimensions of the transverse members, such as for example the length, height and width, can differ from one another.

Returning to FIG. 2, each transverse member 20 is attached to the internal surface $10_2$ of the base 10, and to the walls of the median hole 14. The illustrated transverse members 20 therefore extends along the axis Z-Z approximately over half the thickness of the keel 12. In a variation, however, the thickness of the transverse members 20 may be greater. From this perspective, the transverse members 20 extend, for example, to the lower edge of the keel, having a shape which tapers in the direction of this lower edge in particular of a pyramid type, so as to mate with the internal shape of the anatomical glenoid cavity.

In addition, each transverse member 20 projects, relative to the keel, from a median region 12, thereof. This median region $12_1$ is defined with reference to the longitudinal main axis X-X of the keel 12 to which reference is made above.

Figure 4:
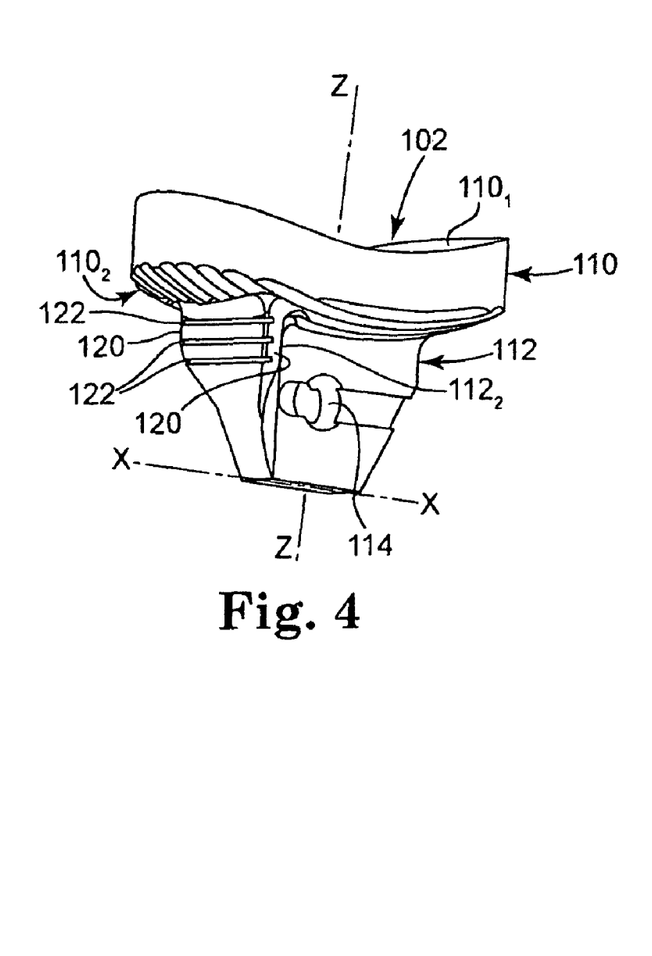
FIG. 4 is a perspective view of a glenoid component with a cross-keeled base in accordance with another embodiment of the present invention.

FIG. 4 illustrates an alternate glenoid component 102 similar to those in FIG. 1 to 3. In the embodiment of FIG. 4, the transverse members 120 project relative to the keel 112 from an end region $112_2$ thereof. This end region is defined, as above for the median region, by reference to the main longitudinal axis X-X of the keel 112. It will be noted that, in this first variation, the angle formed by the transverse members with this main axis X-X is also close to 90°. The transverse member 120 has a height measured along the Z-Z axis generally the same as the height of the keel 112.

In the illustrated embodiment, the transverse member 120 includes a series of grooves 122. Alternatively, a series of anchor members are optionally located on the transverse member 120 (see e.g. FIG. 9). The grooves 122 are provided to increase mechanical stability of the glenoid component 102.

Figure 5:
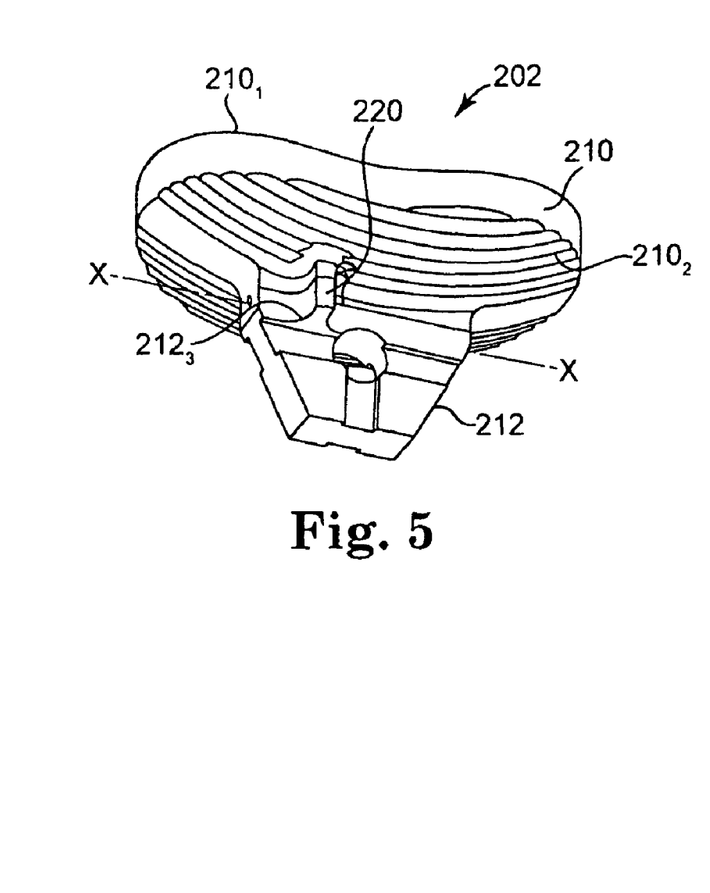
FIG. 5 is a perspective view of a glenoid component with a cross-keeled base in accordance with another embodiment of the present invention.

FIG. 5 illustrates an alternate glenoid component 202 with transverse members 220 that project relative to the keel 212 from an intermediate region $212_3$ thereof, in accordance with an embodiment of the present invention. As in the foregoing, this intermediate region $212_3$ is defined by reference to the main longitudinal axis X-X of the keel 212 located between the respective median region $12_1$ and the end region $112_2$. Similarly to the first two embodiments, the two transverse members 220 form substantially a right angle relative to the main axis X-X of the keel 212.

Figure 6:
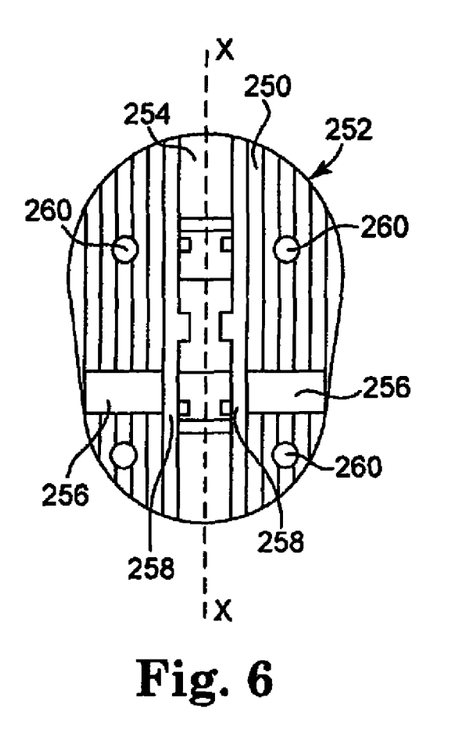
FIG. 6 is a plan view of an alternate glenoid component with transverse members separated from the keel in accordance with an embodiment of the present invention.

FIG. 6 is a plan view of an internal surface 250 of an alternate glenoid component 252 in accordance with an embodiment of the present invention. Keel 254 is similar to the keel 12 in FIG. 3. The transverse members 256, however, are not connected to the keel 254. Rather, gap 258 separates the keel 254 from the transverse members 256. The glenoid component 252 optionally includes a plurality of mounting holes 260 adapted to receive orthopaedic fasteners, such as for example bone screws or pins.

Figure 7:
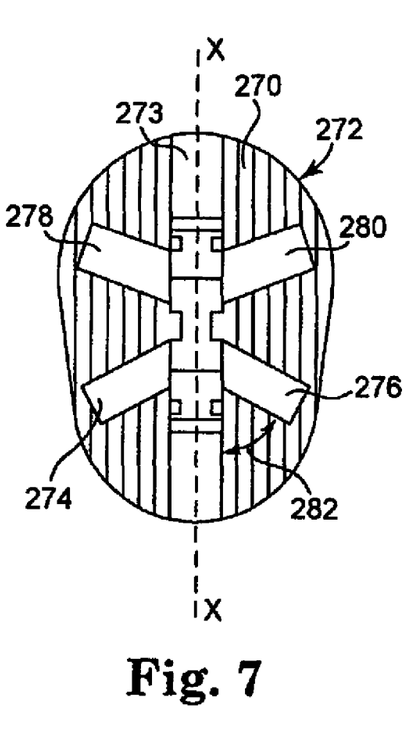
FIG. 7 is a plan view of an alternate glenoid component with angled transverse members in accordance with an embodiment of the present invention.

FIG. 7 is a plan view of an internal surface 270 of an alternate glenoid component 272 in accordance with an embodiment of the present invention. Keel 273 is similar to the keel 12 in FIG. 3. The transverse members 274, 276 are arranged in opposing V-shaped configurations relative to the keel 273. In the illustrated embodiment, transverse members 278, 280 are the mirror image of transverse members 274, 276. The angle 282 formed by the transverse members 274, 276, 278, 280 relative to the axis X-X can vary between about 5 degrees and about 85 degrees. The angle 282 formed with the axis X-X can optionally vary for each of the transverse members 274, 276, 278, 280.

Figure 8:
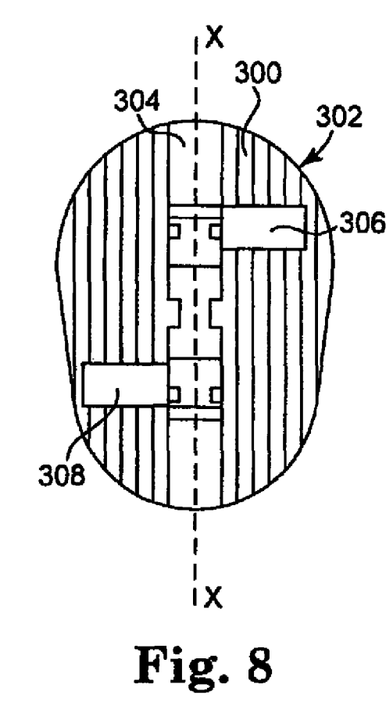
FIG. 8 is a plan view of an alternate glenoid component with asymmetrical transverse members in accordance with an embodiment of the present invention.

FIG. 8 is a plan view of an internal surface 300 of an alternate glenoid component 302 in accordance with an embodiment of the present invention. Keel 304 is similar to the keel 12 in FIG. 3. The transverse members 306, 308 are arranged asymmetrically relative to the axis X-X.

Figure 9:
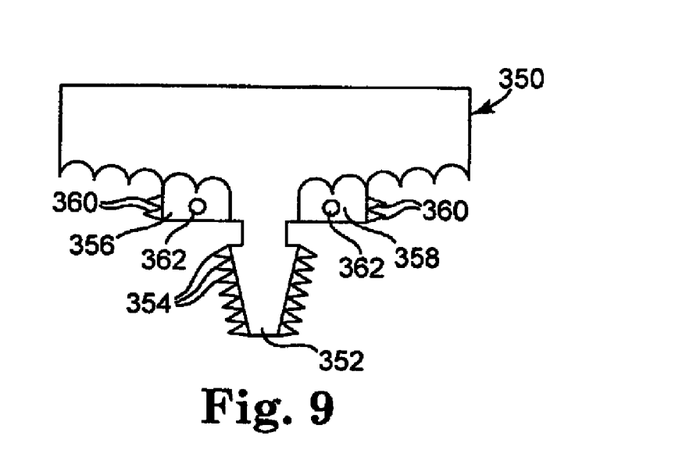
FIG. 9 is a side view of an alternate glenoid component with anchor members in accordance with an embodiment of the present invention.

FIG. 9 is a side view of an alternate glenoid component 350 in accordance with an embodiment of the present invention. Keel 352 is similar to the keel 12 in FIG. 3, except that it includes a series of anchor members 354 arranged generally parallel to axis X-X. Similarly, transverse members 356, 358 include anchor members 360 arranged generally parallel to the axis X-X. The anchor members 354, 360 can include a variety of configurations, such as for example, ridges, protrusions, recesses, serrations, fins, and the like. The anchor members 354, 360 provide enhanced engagement with the bone in the glenoidal cavity. The transverse members 356, 358 optionally include holes 362, similar to the hole 14 made in the keel 12, so as to allow the creation of a cement bridge or a bone bridge.

Figure 10:
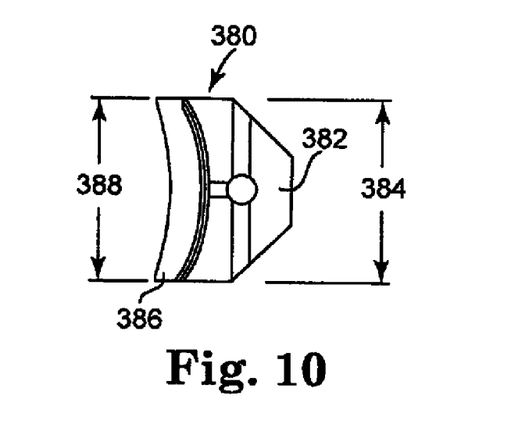
FIG. 10 is a side view of an alternate glenoid component with a keel having a longitudinal length approximately equal to a length of the base plate in accordance with an embodiment of the present invention.
Figure 11:
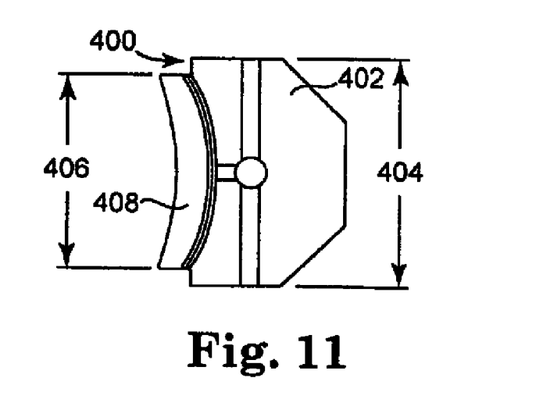
FIG. 11 is a side view of an alternate glenoid component with a keel having a longitudinal length greater than a length of the base plate in accordance with an embodiment of the present invention.

FIG. 10 is a side view of an alternate glenoid component 380 in accordance with an embodiment of the present invention. Keel 382 has a longitudinal length 384 approximately equal to length 388 of the base 386. FIG. 11 is a side view of an alternate glenoid component 400 in accordance with an embodiment of the present invention. Keel 402 has a longitudinal length 404 greater than length 406 of the base 408.

As seen in the foregoing, the relative position and configuration of the transverse members relative to the keel is variable. The transverse members can extend from different positions along the keel at a variety of angles.

The present invention is also directed to a set of glenoid components on which the transverse members have different sizes, shapes, positions and configurations. A set of glenoid components may include transverse members, for example, with heights less than a height of the keel; at non-orthogonal angles relative to the longitudinal axis; integrally formed with, or connected to, the keel; symmetrical or asymmetrical arranged about the longitudinal axis; located at a median region, an intermediate region or an end region of the keel; with a gap between one or more of the transverse members and the keel; with anchor members oriented generally parallel to the longitudinal axis and attached to at least one of the transverse members or the keel; at least one generally planar surface located on the transverse members oriented generally parallel to the external articulating surface; and/or with holes in the transverse members. Variations in the keel configuration may also be incorporated in the set of glenoid components. Depending on the patient's anatomy, determined by the surgeon before and/or during surgery, it is possible to select a glenoid component that is anatomically optimized for the patient.

Optimizing the glenoid component for the patient's anatomy has the advantage of minimizing rocking of the glenoid component and reduces loosening of the glenoid component from the glenoid cavity. In addition, the keel and transverse members increase the rigidity of the base of the glenoid component. This structural advantage allows micro-movements to be reduced, owing to the improvement in the primary grip of the entire component. Finally, transverse members anatomically optimized resist shearing forces applied to the glenoid component better than conventional glenoid components.

The various embodiments of the glenoid components disclosed herein can be used with partial or total anatomical shoulder prostheses or reverse prostheses, such as disclosed in U.S. Publication No. 2005/0278030; 2005/0278031; 2005/0278032; 2005/0278033; 2005/0230197; and 2005/0049709, which are all hereby incorporated by reference.

All of the patents and patent applications disclosed herein, including those set forth in the Background of the Invention, are hereby incorporated by reference. Although specific embodiments of this invention have been shown and described herein, it is to be understood that these embodiments are merely illustrative of the many possible specific arrangements that can be devised in application of the principles of the invention. Numerous and varied other arrangements can be devised in accordance with these principles by those of ordinary skill in the art without departing from the scope and spirit of the invention.

What is claimed is:

1. A glenoid component for a shoulder prosthesis adapted to be mounted in a glenoid cavity of a shoulder, the glenoid component comprising:
   a base comprising an external articulating surface having a continuous arcuate profile configured to cooperate in an anatomical manner with a hemispherical humeral head and an internal surface adapted to engage with the glenoid cavity of the shoulder;
   an elongated keel attached to the internal surface of the base and extending along a longitudinal axis of the base, the keel having a proximal end and a distal end and being adapted to engage with the glenoid cavity; and
   one or more transverse members extending away from the longitudinal axis of the base, the transverse members comprising a maximal proximal-distal dimension less than a dimension between the proximal end and the distal end of the keel and a length less than about half a length of the keel when measured along the longitudinal axis, the transverse members including at least one generally planar surface adapted to contact and engage the glenoid cavity, wherein the generally planar surface is spaced at a distance from the internal surface of the base, and wherein the generally planar surface is oriented generally parallel to the external articulating surface.

2. The glenoid component of claim 1 wherein the transverse members comprise an angle relative to the longitudinal axis of about 30° to about 150°.

3. The glenoid component of claim 1 wherein the transverse members are integrally formed with, or connected to, the keel.

4. The glenoid component of claim 1 wherein the transverse members comprise a length perpendicular to the longitudinal axis greater than approximately one-half of a thickness of the keel.

5. The glenoid component of claim 1 wherein the transverse members comprise a symmetrical configuration about the longitudinal axis.

6. The glenoid component of claim 1 wherein the transverse members comprise an asymmetrically configuration relative to the longitudinal axis.

7. The glenoid component of claim 1 wherein the transverse members extend from a median region of the keel.

8. The glenoid component of claim 1 wherein the transverse members extend from an end region of the keel.

9. The glenoid component of claim 1 wherein the transverse members extend from an intermediate region of the keel.

10. The glenoid component of claim 1 wherein the keel comprises a length approximately greater than or equal to a length of the base portion, as measured along the longitudinal axis.

11. The glenoid component of claim 1 comprising at least one generally planar surface located on at least one of the elongated keel or one of the transverse members, the planar surface oriented generally parallel to the external articulating surface.

12. The glenoid component of claim 1 comprising a gap between one or more of the transverse members and the keel.

13. The glenoid component of claim 1 comprising anchor members oriented generally parallel to the longitudinal axis and attached to at least one of the transverse members or the keel.

14. The glenoid component of claim 1 comprising holes in the transverse members.

15. The glenoid component of claim 1 wherein the base comprises holes adapted to receive orthopaedic fasteners.

16. The glenoid component of claim 1 wherein the transverse members comprise non-orthogonal angles relative to the longitudinal axis.

17. Total shoulder prosthesis comprising:
   the glenoid component of claim 1; and
   a prosthetic humeral component adapted to cooperate with the external articulating surface.

18. The glenoid component of claim 1 comprising: a first glenoid component with one or more transverse members in a first configuration relative to the longitudinal axis; and second glenoid component with one or more transverse members in a second configuration relative to the longitudinal axis, wherein the first configuration is different from the second configuration.

19. A glenoid component for a shoulder prosthesis adapted to be mounted in a glenoid cavity of a shoulder, the glenoid component comprising:
   a base comprising an external articulating surface having a continuous arcuate profile configured to cooperate in an anatomical manner with a hemispherical humeral head and an internal surface adapted to engage with the glenoid cavity of the shoulder;
   an elongated keel attached to the internal surface of the base and extending along a longitudinal axis of the base; and
   a transverse members defining an intersection with the base and extending in a transverse direction away from the longitudinal axis of the base, the transverse members comprising a length measured along the transverse direction that is less than about half a length of the keel measured along the longitudinal axis and having an engagement surface adapted to engage the glenoid cavity, wherein at the intersection the engagement surface is located at an intermediate position between the internal surface of the base and a distal end of the keel and wherein the engagement surface is oriented generally parallel to the external articulating surface.

20. A glenoid component for a total shoulder prosthesis, comprising:
   a base having a first face adapted for engaging a glenoid cavity of a shoulder and a second face positioned opposite the first face and having an arcuate profile adapted for articulation with a humeral head, the base having a length along a longitudinal axis;
   a keel extending distally from a zone of connection with the base and being adapted for securing the glenoid component in the glenoid cavity, the keel defining a length along the longitudinal axis and a thickness extending distally along a Z-axis,
   a transverse member extending distally from the base and laterally from the longitudinal axis,
   wherein the length of the keel in the region of the zone of connection with the base is less than the length of the base and the transverse member has a maximum thickness along the Z-axis that is approximately half the thickness of the keel.

21. A glenoid component for a shoulder prosthesis adapted to be mounted in a glenoid cavity of a shoulder, the glenoid component comprising:

a base comprising an external articulating surface having a continuous arcuate profile configured to cooperate in an anatomical manner with a hemispherical humeral head and an internal surface adapted to engage with the glenoid cavity of the shoulder;

an elongated keel attached to the internal surface of the base and extending along a longitudinal axis of the base, the keel having a length along the longitudinal axis of the base and being adapted to engage with the glenoid cavity; and a transverse member extending in a transverse direction from the longitudinal axis of the base, the transverse member having a length along the transverse direction, where a maximum height of the transverse member is less than a maximum height of the keel and the length of the transverse member along the transverse direction is less that about half the length of the keel along the longitudinal axis, the transverse member including a surface spaced at a distance from the internal surface of the base and adapted to contact and engage the glenoid cavity.

* * * * *